United States Patent [19]
Portoghese et al.

[11] Patent Number: 5,352,680
[45] Date of Patent: Oct. 4, 1994

[54] DELTA OPIOID RECEPTOR ANTAGONISTS TO BLOCK OPIOID AGONIST TOLERANCE AND DEPENDENCE

[75] Inventors: Philip S. Portoghese, St. Paul; Akira E. Takemori, Edina, both of Minn.

[73] Assignee: Regents of the University of Minnesota, Minneapolis, Minn.

[21] Appl. No.: 914,448

[22] Filed: Jul. 15, 1992

[51] Int. Cl.$^5$ .................................... A61K 31/485
[52] U.S. Cl. .................................... 514/279
[58] Field of Search .......................... 514/279

[56] References Cited

U.S. PATENT DOCUMENTS

| | | | |
|---|---|---|---|
| 4,440,932 | 4/1984 | Kotick et al. | 546/44 |
| 4,761,429 | 8/1988 | Blum et al. | 514/561 |
| 4,816,586 | 3/1989 | Portoghese | 544/340 |
| 4,882,335 | 11/1989 | Sinclair | 514/282 |
| 5,086,058 | 2/1992 | Sinclair | 514/282 |

FOREIGN PATENT DOCUMENTS

WO85/00970 3/1991 PCT Int'l Appl. .

OTHER PUBLICATIONS

J. S. Shaw et al., Life Sci., 31, 1259 (1982).
R. Cotton et al., Eur. J. Pharmacol., 97, 331 (1984).
P. S. Portoghese et al., J. Med. Chem., 31, 281 (1988).
P. S. Portoghese et al., J. Med. Chem., 33, 1547 (1990).
P. S. Portoghese et al., Eur. J. Pharmacol., 146, 185 (1988).
E. E. Abdelhamid et al., J. Pharmacol. Exp. Ther., 258, 299 (1991).
M. Gates et al., J. Med. Chem., 7, 127 (1964).
P. S. Portoghese et al., J. Med. Chem., 34, 1292 (1991).
T. J. Haley et al., Brit. J. Pharmacol., 12, 12 (1957).
E. L. Way et al., J. Pharmacol. Exp. Ther., 167 1 (1969).
I. Yano et al., Res. Commun. Chem. Pathol. Pharmacol., 16, 721 (1977).
G. Hayashi et al., Eur. J. Pharmacol., 16, 63 (1971).
P. S. Portoghese et al., J. Med. Chem., 23 233 (1980).
A. E. Takemori et al., Eur. J. Pharmacol., 70, 445 (1981).
S. J. Ward et al., J. Pharmacol. Ther., 220, 494 (1982).
G. E. DeLander et al., J. Pharmacol. Exp. Ther., 231, 91 (1984).
Q. Jiang et al., J. Pharmacol. Exp. Ther., 257, 1069 (1991).
M. Sofuoglu et al., J. Pharmacol. Exp. Ther., 257, 676 (1991).
P. S. Portoghese et al., J. Med. Chem., 33, 1714 (1990).
A. E. Takemori et al., J. Pharmacol. Exp. Ther., 246, 255 (1988).
A. E. Takemori et al., J. Pharmacol. Exp. Ther., 243, 91 (1987).
J. C. Froehlich et al., Alcoholism, Clin. Exp. Res., 15, 315, Abstract 20 (Apr. 1991).
J. C. Froehlich et al., Pharmacol. Biochem. Behavior, 35, 385 (1990).
J. C. Froelich et al, Psychopharmacol., 103, 467 (1991).
M. S. Yamamura et al., Life Sci., 50, PL119 (1992).
H. P. Rang, Brit. J. Pharmacol., 22, 356 (1964).
J. R. Volpicelli et al., Opioids, Bulimia and Alcohol: Abuse and Alcoholism, L. D. Reid, ed., Springer-Verlag, Pub. (1990) at pp. 195-214.
L. L. Werling et al., J. Pharmacol. Exp. Ther., 233, 722 (1985).
J. J. Gormley et al., Life Sci., 31, 1263 (1982).
J. S. Shaw et al., Life Sci., 31, 1259 (1982).
W. R. Martin, Pharmacol. Rev., 35, 283 (1984).

Primary Examiner—Marianne M. Cintins
Assistant Examiner—William R. A. Jarvis
Attorney, Agent, or Firm—Warren D. Woessner

[57] ABSTRACT

A motion provided to alleviate the tolerance to, or dependence on, an opiate analgesic, by the administration of an effective amount of a selective delta opioid receptor antagonist to a human patient in need of such treatment.

23 Claims, 4 Drawing Sheets

Fig. 1

DELTA OPIOID RECEPTOR ANTAGONISTS TO BLOCK OPIOID AGONIST TOLERANCE AND DEPENDENCE

BACKGROUND OF THE INVENTION

This invention was made with the assistance of the Government under a grant from the Public Health Service (ADAMHA Grant No. 5RO1DA 06251). The U.S. Government has certain rights in the invention.

The opium group of narcotic drugs are among the most powerfully acting and clinically useful drugs producing depression of the central nervous system. Drugs of this group are used principally as analgesics, but possess numerous other useful properties. Morphine, for example, is used to induce sleep in the presence of pain, check diarrhea, suppress cough, ease dyspnea, and facilitate anesthesia.

Unfortunately, morphine also depresses respiration; it increases the activity and tone of the smooth muscles of the gastrointestinal, biliary, and urinary tracts causing constipation, gallbladder spasm, and urinary retention; it causes nausea and vomiting in some individuals; and it may induce cutaneous pruritus. In addition to these actions, morphine and related compounds have other qualities which tend to limit their usefulness. Tolerance to the analgesic effect develops over a period of time so that the dose must be increased periodically to obtain equivalent pain relief. Tolerance and physical dependence develop, which combined with euphoria result in excessive use; leading to the risk of fatal overdosing, and addiction of those patients who have susceptible personalities.

The fact that the effects of endogenous opioids such as the enkephalins and exogenous opioids are mediated by at least three different types [mu ($\mu$), delta ($\delta$), kappa ($\kappa$)] of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side effects mediated through other opioid receptor types can potentially be minimized or eliminated.

The prototypical opioid antagonists, naloxone and naltrexone, are used primarily as pharmacologic research tools and for the reversal of toxic effects of opioids in case of overdose. Since these antagonists act at multiple opioid receptors, their application in other therapeutic areas or as pharmacologic tools appear to be limited.

Some progress has been made in the development of highly selective opioid antagonists. For example, Portoghese et al. (U.S. Pat. No. 4,816,586) disclose certain opiate analogs which possess high selectivity and potency at delta receptors. Minimal involvement was observed at mu and kappa opioid receptors. Pentapeptides structurally related to the enkephalins have also been reported to be highly delta-selective opioid antagonists. Such compounds (e.g., ICI 174864) currently are employed as pharmacologic probes of receptor function and structure, but they possess the disadvantage of low potency and poor penetration into the central nervous system (CNS). See J. W. Shaw et al., *Life Sci.*, 31, 1259 (1982) and R. Cotton et al., *Eur. J. Pharmacol.*, 97,331 (1984).

Thus, a continuing need exists for pharmacological approaches to the treatment of opioid dependence. More specifically, a need exists for an effective method to prevent morphine tolerance and/or dependence, using specific and potent opioid receptor antagonists, having a prolonged duration of action.

SUMMARY OF THE INVENTION

The present invention provides a method for treating (blocking or reducing) the tolerance and dependence caused by the administration of an opioid agonist, such as the opioid analgesics, to a human in need of such treatment, comprising administering to said human a pharmaceutical unit dosage form comprising an effective amount of a compound of the formula I:

wherein $R^1$ is $(C_1-C_5)$alkyl, $C_3-C_6$(cycloalkyl)alkyl, $C_5-C_7$-(cycloalkenyl)alkyl, aryl, aralkyl, trans($C_4-C_5$-)alkenyl, allyl or furan-2-ylalkyl, $R^2$ is H, OH or $O_2C(-C_1-C_5)$alkyl; $R^3$ is H, $(C_1-C_5)$alkyl or $(C_1-C_5)$alkyl CO; X is O, S or NY, wherein Y is H or $(C_1-C_5)$alkyl; and $R^4$ and $R^5$ are individually H, F, Cl, Br, NCS, $NO_2$, $NH_2$, $(C_1-C_5)$alkyl, $(C_1-C_5)$alkoxy or together are benzo; and the pharmaceutically acceptable salts thereof.

A preferred compound of formula I, disclosed in U.S. Pat. No. 4,816,586, has been named "naltrindole" or "NTI" (17-(cyclopropylmethyl)-6,7-dehydro-3,14$\beta$-dihydroxy-4,5$\alpha$-epoxy-6,7-2',3'-indolmorphinan) and has the formula:

Another preferred compound of formula I is (17-(cyclopropylmethyl) -6,7-dehydro-3,14$\beta$-dihydroxy-4,5$\alpha$-epoxy-6,7-2',3'-benzo[b]furanomorphinan. See P. S. Portoghese et al., *J. Med. Chem.*, 31, 281 (1988). Another preferred compound of formula I is naltrindole 5'-isothiocyanate or "5'-NTII" (see, P. S. Portoghese et al., *J. Med. Chem.*, 33, 1547 (1990); *Eur. J. Pharmacol.*, 146, 185 (1988); *J. Med. Chem.*, 31, 281 (1988); *J. Pharmacol. Exp. Ther.*, 258, 299 (1991)). These compounds are selective $\delta$-opioid receptor antagonists.

In another embodiment of the present method, a human patient at risk of developing morphine tolerance or dependence is treated with an effective amount of a compound of the formula (II):

(II)

wherein $R^1$ is $(C_1-C_5)$alkyl, $C_3-C_6$(cycloalkyl)alkyl, $C_5-C_7$-(cycloalkenyl)alkyl, aryl, aralkyl, trans$(C_4-C_5)$alkenyl, allyl or furan-2-ylalkyl, $R^2$ is H, OH or $O_2C(-C_1-C_5)$alkyl; $R^3$ is H, $(C_1-C_5)$alkyl or $(C_1-C_5)$alkylCO; and $R^4$ and $R^5$ are individually H, F, Cl, Br, $NO_2$, $NH_2$, NCS, $(C_1-C_5)$alkyl, $(C_1-C_5)$alkoxy or together are dioxymethylene (—$OCH_2O$—) or benzo; and the pharmaceutically acceptable salts thereof.

The compounds of formula II are selective for the $\delta_1$ subset of delta receptors. Thus, the compounds of formula II can also be used as pharmacological and biochemical probes of opiate receptor structure and function, e.g., to measure the selectivity of other opioid receptor antagonists or agonists.

The present invention also provides a method of treating morphine tolerance and dependence by administering effective amounts of a biologically active compound of formula III:

wherein $R^1$ is $(C_1-C_5)$alkyl, $C_3-C_6$(cycloalkyl)alkyl, $C_5-C_7$-(cycloalkenyl)alkyl, aryl, aralkyl, trans$(C_4-C_5)$alkenyl, allyl or furan-2-ylalkyl, $R^2$ is H, OH or $O_2C(-C_1-C_5)$alkyl; $R^3$ is H, $(C_1-C_5)$alkyl or $((C_1-C_5)$alkyl)-C=O; M is N or CH, and $R^4$ and $R^5$ are as described for formula I hereinabove; and the pharmaceutically acceptable salts thereof.

The compounds of formulas I, II or III may also be useful to inhibit the respiratory depression caused by certain opioid agonists without inhibiting their analgesic action.

The alkyl moiety present in the $R^1$ group which links the cycloalkyl, cycloalkenyl, aryl, or furan-2-yl moiety to the basic nitrogen atom in the compounds of formulas I, II or III is a lower(alkyl) group, preferably —$(CH_2)_n$—, wherein n is about 1–5, most preferably n is 1, e.g., $R^1$ is $C_3-C_6$(cycloalkyl)methyl, $C_1-C_7$(cycloalkenyl)methyl, arylmethyl or furan-2-ylmethyl. Preferred aryl moieties include $(C_6-C_{10})$aryl, i.e., phenyl, benzyl, tolyl, xylyl, anisyl and the like.

In formulas I, II or III, the position of the —$R^4$ and —$R^5$ groups indicate that they can be either ortho, meta, or para to the —X group or the —N=group, respectively, e.g., $R^4$ and/or $R^5$ can occupy any available site on the phenyl ring. In structure I and II, a bond designated by a wedged or darkened line indicates one extending above the plane of the phenyl rings. A bond designated by a broken line indicates one extending below the plane of the phenyl rings.

These delta-opioid antagonists include compounds of the formula I, formula II or formula III, wherein $R^1$ is $(C_1-C_5)$alkyl, $C_3-C_6$(cycloalkyl)alkyl or $C_5-C_7$(cycloalkenyl)-alkyl, preferably wherein $R^1$ is $C_3-C_6$(cycloalkyl)methyl, and most preferably wherein $R^1$ is cyclopropylmethyl. $R^2$ is preferably OH or OAc ($O_2CCH_3$), and $R^3$ preferably is H. Preferably, at least one, and most preferably, both of $R^4$ and $R^5$ are H, or $R^4$ is H and $R^5$ is NCS, i.e., 5'-NCS. Preferred compounds also result when $R^4$ is H and $R^5$ is F, $(C_1-C_5)$alkyl or $(C_1-C_5)$alkoxy.

For example, in one assay, indole I, where $R^1$ is cyclopropylmethyl, X=NH, $R^2$ is OH, $R^3$ is H, $R^5$ is H and $R^4$ is H, "naltrindole hydrochloride" or "NTI" is at least 500 times more potent than the peptide delta antagonist, ICI 174864, and is more selective than the structurally unrelated opiate M8008. Since the compounds of the invention are formally morphinan derivatives, it is believed that their ability to cross the "blood-brain barrier" and to affect the CNS should be far superior to peptide delta opioid antagonists.

Pharmaceutically acceptable salts of the opioid agonists include salts of organic and inorganic acids, e.g., the sulfate, lactate, nitrate, phthlate pentahydrate, tartrate trihydrate, citrate, valerate, hydrobromide, hydrochloride, methylbromide, mucate and oleate salts.

Although exemplified with reference to morphine, the method of the present invention is also effective with the opioid agonists such as meperidine, oxymorphone, hydromorphone, hydrocodone, oxycodone, levophanol, as well as with diacetylmorphine, morphine-N-oxide, codeine, methadone, fentanyl, sulfentanil, levo-acetylmethadol, alfentanil, levorphanol, tilidine, diphenoxylate, hydroxymorphone, noroxymorphone, metapon, propoxyphene, heterocodeine and the like, and the pharmaceutically acceptable salts thereof.

Although opioid agonists are primarily employed as analgesics, they also have found utility as antitussives, antidiarrhea agents, anesthetics, tranquilizers, and in the management of opium alkaloid addiction.

Preferably, one or more compounds of formula I, II or III are administered to a human patient in conjunction with the administration of one or more of these opioid agonists, preferably morphine or a pharmaceutically acceptable salt thereof. Also, an effective amount of one or more of the present compounds may be combined with an effective amount of morphine, a pharmaceutically acceptable salt thereof and/or another opiate analgesic, in a single combination unit dosage form, such as a tablet, capsule, unit volume of infusable or injectable fluid, and the like, so that the analgesic and the delta-opioid antagonist are administered simultaneously to the patient.

A further aspect of the present invention comprises an article of manufacture comprising packaging material, such as a carton, envelope, bottle, vial, intravenous bag and the like, and at least one pharmaceutical unit dosage form comprising an amount of a compound of formula I, II or III, effective to treat opiate tolerance or dependence in a human due to administration of an opiate analgesic, i.e., morphine or a pharmaceutically acceptable salt or derivative thereof, to said human; and wherein said packaging material comprises instruction means therein or thereon, such as a printed label, package insert, tag, cassette tape, videotape and the like, which indicates that said unit dosage form can be used to treat (reduce or block) opiate tolerance or dependence, or respiratory depression, due to the administration of the opiate analgesic to a human. The packaging material can alternatively comprise one or more of the combination unit dosage forms described hereinabove.

DETAILED DESCRIPTION OF THE INVENTION

Chemistry

Figure 1:
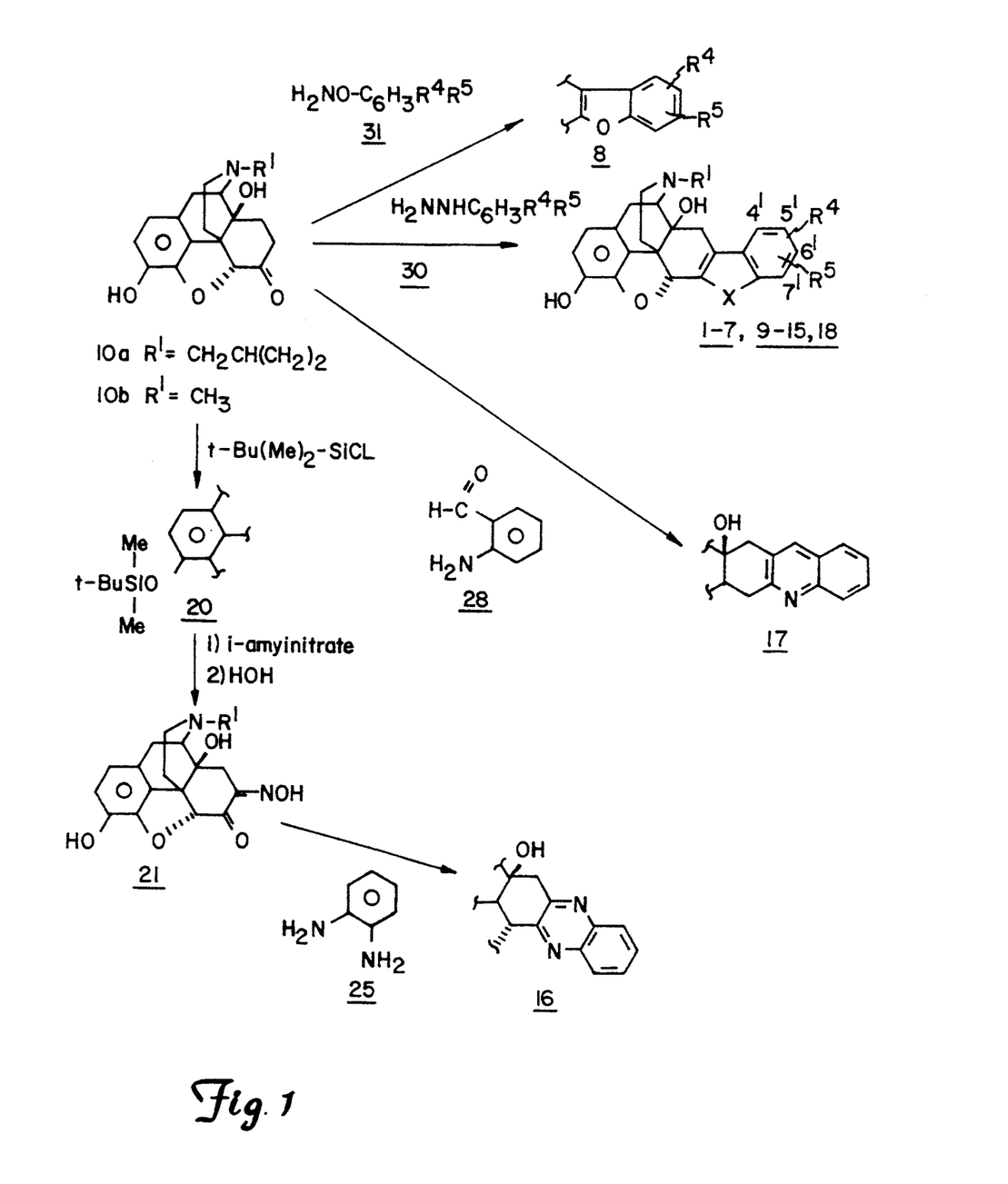
FIG. 1 is a schematic depiction of the synthesis of compounds of formula I and formula III.

Representative compounds of formula I (1–15 and 18) or formula III (16–17) were synthesized from starting materials of formula 10a or 10b as outlined in FIG. 1. The structures of compounds 1–15 and 18, shown generally in FIG. 1, are summarized on Table I, below.

TABLE I

| Compound No. of Table I | $R^1$ | X | $R^4$ | $R^5$ |
|---|---|---|---|---|
| 1 | $CpCH_2$[1] | NH | H | H |
| 2 | $CpCH_2$ | $NCH_3$[2] | H | H |
| 3 | $CpCH_2$ | NH | H | 5'-F |
| 4 | $CpCH_2$ | NH | H | 5'-$OCH_3$ |
| 5 | $CpCH_2$ | NH | H | 5'-$CH_3$ |
| 6 | $CpCH_2$ | NH | H | 5'-$NO_2$ |
| 7 | $CH_3$ | NH | H | H |
| 8 | $CpCH_2$ | O | H | H |
| 9[3] | $CpCH_2$ | NH | H | 5'-OH |
| 10 | $CpCH_2$ | NH | H | 4'-F |
| 11 | $CpCH_2$ | NH | H | 7'-F |
| 12 | $CpCH_2$ | NH | H | 4' and 6'-$CH_3$ (mixture) |
| 12a | $CpCH_2$ | NH | H | 5'-$NH_2$ |
| 12b | $CpCH_2$ | NH | H | 5'-NCS |
| 13 | $CpCH_2$ | NH | H | 7'-$CH_3$ |
| 14 | $CpCH_2$ | NH | H | 7'-$OCH_3$ |
| 15[4] | $CpCH_2$ | NH | H | 7'-OH |
| 18 | $CpCH_2$ | NH | 6'-CH=CH—CH=CH-7' | |

[1]Cyclopropylmethyl.
[2]From Fischer indole synthesis of 10a + $H_2NN(CH_3)Ph$.
[3]Derived from 4 using five equivalents of $BBr_3$.
[4]Hydrolysis product formed during synthesis of 14.

Compounds 1–18 have either indole (1–7, 9–15), benzofuran (8), benzopyrazine (16), benzoquinoline (17) or benzoindole (18) moieties, fused to the 6,7-position of the opiate C-ring.

Starting Materials

The structures, con, non names and Merck Index reference numbers of representative 4,5-epoxy-6-ketomorphinan starting materials of general formula 10 are summarized on Table II, below.

TABLE II

| Compound | $R^1$ | $R^2$ | $R^3$ | Common Name | Merck No.[2] |
|---|---|---|---|---|---|
| 10a | $CH_2CH(CH_2)_2$ | OH | H | naltrexone | 6209 |
| 10b | $CH_3$ | OH | H | oxymorphone | 6837 |
| 10c | $CH_3$ | H | H | hydromorphone | 4714 |
| 10d | $CH_3$ | H | $CH_3$ | hydrocodone | 4687 |
| 10e[1] | $CH_2CH(CH_2)_2$ | H | H | — | — |
| 10f | $CH_2CH=CH_2$ | OH | H | naloxone | 6208 |
| 10g | $CH_3$ | OH | $CH_3$ | oxycodone | 6827 |

[1]Preparation, M. Gates et al., J. Med. Chem., 7, 127 (1964).
[2]The Merck Index, W. Windholz, ed., Merck & Co., Rahway, NJ (10th ed. 1983).

Other starting materials of formula 10 can be prepared by synthetic methods which are well known in the art of organic chemistry. For example, compounds of formula 10 wherein $R^1$ is H and $R^3$ is a suitable protecting group, and wherein the 6-keto group has also been protected, can be prepared from compounds 10a–q. These intermediates can be N-alkylated and deprotected to yield compounds of formula I wherein $R^1$ is $C_2$–$C_5$(alkyl), $C_4$–$C_6$(cycloalkyl)alkyl, $C_5$–$C_7$(cycloalkenyl)alkyl, aryl, aralkyl, trans-$C_4$–$C_5$-alkenyl or furan-2-ylakyl, by the application of well known reactions.

For example, the free hydroxyl groups of compounds of formula 10, e.g., $R^2$=OH and/or $R^3$=H, can be protected by acid-labile groups such as tetrahydropyranl-yl, trimethyl-silyl, 1-methoxy-isopropyl and the like as disclosed in *Compendium of Organic Synthetic Methods*, I. T. Harrison et al., eds., Wiley-Interscience, New York, N.Y. (1971) at pages 124–131, (hereinafter "Compendium"), the disclosure of which is incorporated by reference herein. The protection of the 6-keto group of compounds of formula 10 by its reversible conversion into a ketal or a thioketal group is disclosed in Compendium, at pages 449–453, the disclosure of which is incorporated by reference herein. Methods for the demethylation of N-methyl amines have been disclosed, for example, in Compendium at page 247, *J. Amer. Chem. Soc.*, 89, 1942 (1967) and *J. Amer. Chem. Soc.*, 77, 4079 (1955), the disclosures of which are incorporated by reference herein.

Procedures for the alkylation of secondary amines with halides under basic or neutral conditions are well known. For example, see Compendium at pages 242–245; *Org. Synth.*, 43, 45 (1963); *J. Org. Chem.*, 27, 3639 (1962) and *J. Amer. Chem. Soc.*, 82, 6163 (1960), the disclosures of which are incorporated by reference herein.

Compounds of formula I or III wherein $R^2$ is acyloxy and/or $R^3$ is acyl can be prepared by using the corresponding starting material 10. For example, starting material 10a can be diacylated by reacting it with the appropriate ($C_1$-$C_5$)alkyl anhydride in pyridine for 10-18 hrs at 18°-25° C. The resultant 3,14-diacylated compound can be converted to the 14-acylated compound by limited hydrolysis. The 3-acylated starting materials can be prepared by the short-term reaction of the compound of formula 10 with the anhydride, e.g., for about 2-4 hours. The 3-acylated product can be separated from the 3,14-diacylated product by chromatography.

Synthesis of Delta Opioid Receptor Antagonists

The preparation of 1-7, 9-15 and 18 was accomplished using the Fischer indole synthesis. See R. B. Van Orden et al., Chem. Rev., 30, 78 (1942), the disclosure of which is incorporated by reference herein. A compound of formula 10, e.g., naltrexone hydrochloride (10a·HCl) or oxymorphone hydrochloride (10b·HCl) and the appropriate aromatic hydrazine hydrochloride (30) were refluxed in glacial acetic acid or methanol containing an organic or inorganic acid such as methanesulfonic acid or hydrochloric acid (HCl) for 3-6 hours. Compound 12b was prepared by reducing 5'-nitroindole (6) to the 5'-amino derivative 12a, which was treated with thiophosgene to yield 12b, as the hydrated salt. See P. S. Portoghese et al., J. Med. Chem., 31, 281 (1988). The 6',7'-benzo-derivative (18), was prepared by refluxing naltrexone·HCl with 1-napthylhydrazine.

Benzofuran 8 was prepared by refluxing an ethanol solution containing equivalent amounts of 10a·HCl, methane sulfonic acid and o-phenylhydroxylamine·HCl (31) for 18 hours.

The benzopyrazine 16 was synthesized from 10a·HCl by a conversion to the oximino derivative 51 followed by reaction with o-phenylenediamine 25.

The quinoline derivative 17 was prepared by refluxing naltrexone·HCl with o-aminobenzaldehyde 28 and methanesulfonic acid in ethanol. The corresponding benzothiophene derivatives (I, X=S) can be synthesized by reacting a compound of formula 10 with thiophenol in the presence of an acid, followed by photolysis of the OH-protected thioenol under a nitrogen atmosphere using a Hg high pressure lamp (see S. H. Green et al., J. Org. Chem., 33, 2218 (1968), the disclosure of which is incorporated by reference herein).

The acid salts of compounds of formulas I, II, or III wherein $R^3$=H can be converted into the corresponding ($C_1$-$C_5$)alkoxy derivatives [$R^3$=($C_1$-$C_5$)alkyl] by dissolving the starting material in DMF and adding an excess of the appropriate ($C_1$-$C_5$)alkyl iodide and an amine such as diisopro-pylethylamine. The reaction can be conducted at an elevated temperature for about 4-10 hours. The final product can be purified by column chromatography.

Pharmaceutically acceptable amine salts of these compounds may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like.

These physiologically acceptable salts are prepared by methods known in the art, e.g., by dissolving the free amine bases with an excess of the acid in aqueous alcohol.

The synthesis of compounds 1-12 and 13-17 is set forth in detail in P. S. Portoghese (U.S. Pat. No. 4,816,586), the disclosure of which is incorporated by reference herein.

The compounds of formula II can be readily synthesized by reacting a compound of formula 10 with benzaldehyde or a mono- or di-substituted derivative thereof in the presence of base, as shown below.

wherein $R^1$, $R^2$, $R^3$, $R^4$ and $R^5$ are as disclosed hereinabove. Preferably, II is naltrexone hydrochloride, e.g., $R^3$=H, $R^2$=OH and $R^1$ is cyclopropylmethyl, and the synthesis of compound II wherein $R^2$=OH, $R^1$=cyclopropylmethyl and $R^3$=$R^4$=$R^5$=H is carried out as described by P. S. Portoghese et al., J. Med. Chem., 34, 1292 (1991). When $OR^3$ and/or $R^2$ are base-liable groups such as alkanoxy, $R^3$ may be H and $R^2$ may be OH in the compound of formula II. In such situations, the protecting groups can be replaced by art-recognized methodologies for the protection/deprotection of hydroxyl groups. Of course, if naltrexone·HCl or a similar compound of formula 10, comprising free OH groups is used to prepare compounds of formula II wherein $R^3$ is H and/or $R^2$ is OH or H, the free hydroxyl groups in the compound of formula II can be also converted to alkanoyloxy groups by methods known to the art.

Administration and Dosage Forms

In the clinical practice of the present method, the compounds of the present invention will normally be administered orally or parenterally, as by injection or infusion, in the form of a pharmaceutical preparation comprising the active ingredient in combination with a pharmaceutically acceptable carrier, e.g., in the form of a pharmaceutical unit dosage form. The carrier may be a solid, semi-solid or liquid diluent or be compressed or shaped into an ingestible capsule. The compound or its salt may also be used without carrier material. Examples of pharmaceutical unit dosage forms comprising the present antagonists include tablets, pre-selected volumes of intravenous solutions, suspensions, hard or soft gelatin capsules, microcapsules, liposomes and the like. Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

As mentioned hereinabove, an effective amount of a compound or compounds of formulas I, II or III can also be combined in a single unit dosage form with an effective amount of an opioid agonist, such as a mu receptor selective opiate analgesic. As noted above, preferred analgesics of this class include morphine and its pharmaceutically acceptable salts and derivatives, including morphine hydrochloride, morphine-N-oxide, morphine sulfate, codeine, heroin, oxymorphone, hydromorphone, hydrocodone and the like.

Effective analgesic amounts of morphine and its salts are well known to the art. For example, morphine sulfate is commonly injected into an adult human at 10 mg every four hours, or 12–120 mg daily. Pediatric, s.c. dosages are 0.1–0.2 mg/kg up to a maximum of 15 mg/dose. Injectable morphine sulfate preparations comprise those of 8, 10 and 15 mg/ml of aqueous vehicle.

Dosages of a given compound of formulas I, II or III which are effective to counteract the tolerance and/or dependence of morphine, a morphine salt or other opiate analgesic can be extrapolated, to some extent, from the murine data disclosed hereinbelow, by methods known to the art for extrapolation of animal dosing data to humans. For example, see U.S. Pat. Nos. 5,035,878 and 4,938,949.

The invention will be further described by reference to the following detailed examples, wherein morphine sulfate was obtained from Cambridge Research Biochemicals Ltd. (Atlantic Beach, N.Y.). Naloxone hydrochloride was a gift from Endo Laboratories, Inc. (Garden City, N.Y.). DAMGO and DSLET were purchased from Bachem Fine Chemicals, Inc. (Torrance, Calif.) and Serva Biochemicals (Westbury, N.Y.), respectively. Drugs given i.c.v. were administered in a volume of 5 μl and those given s.c. were administered in a volume of 10 ml/kg, in accord with T. J. Haley et al., *Br. J. Pharmacol.*, 12, 12 (1957).

Male Swiss-Webster mice (BioLab, White Bear Lake, Minn.) weighing 20 to 25 g were used. The mice were rendered tolerant to and dependent on morphine by s.c. implantation of one morphine pellet (75 mg free base)/mouse for 3 days according to the procedure of E. L. Way et al., *J. Pharmacol. Exp. Ther.*, 167, 1 (1969). Control animals were implanted with placebo pellets. Mice were anesthetized lightly with methoxyflurane during the implantation process. Mice were made acutely tolerant and dependent by a single s.c. injection of 100 mg/kg of morphine sulfate 4 hr before testing, as disclosed by I. Yano et al., *Res. Commun. Chem. Pathol. Pharmacol.*, 16, 721 (1977).

The degree of morphine tolerance was monitored by determining the $ED_{50}$ of morphine sulfate in the modified tail-flick antinociceptive assay as disclosed by G. Hayashi et al., *Eur. J. Pharmacol.*, 16, 63 (1971). An antinociceptive ("pain blocking") response was considered to occur when an individual animal displayed a latency that was greater than its control reaction time plus three S.D.s of the control mean reaction time of all animals in the group. At least 30 mice (10/group) and three to four dose levels were used to determine each $ED_{50}$ value.

The degree of physical dependence on morphine was assessed by estimating the amount of the morphine antagonist, naloxone, required to induce withdrawal jumping. E. L. Way et al., cited above, have shown that there is an inverse relationship between the degree of dependence and the amount of naloxone required to precipitate withdrawal jumping in mice. Morphine-treated mice were placed singly into 30×30 cm Plexiglas cylinders immediately after s.c. injection of various doses of naloxone. The number of vertical jumps by the animal during a 15-minute observation period was recorded. The criterion for a positive jumping response was that a mouse was required to jump more than 4 times during the observation period. (See, I. Yano et al., cited above). The $ED_{50}$ of naloxone for inducing withdrawal jumping was estimated by the up and down method of Dixon using six animals for each determination. The method of W. J. Dixon, *Am. Stat. Assoc. J.*, 69., 967 (1965), is a quantal assay for sample sizes of $\leq$ six animals. This assay uses sequentially determined dose levels and sequentially determined sample sizes. The assay is particularly useful for small sample sizes and in cases in which the approximate range of the $ED_{50}$ value is unknown. If the assay is repeated several times (4 times with different animals in this study), then the resulting $ED_{50}$ values can be expressed as mean $\pm$S.E.

The $ED_{50}$ values of morphine and their 95% CL were determined by the parallel line assay of D. J. Finney, *Statistical Methods in Biological Assay*, Hafner Pub. Co., N.Y. (2d ed. 1969) with the aid of a computer program which has the capability to analyze at the same time 12 lines (dose-response curves) and 6 points (dose levels) per line with log and probit transformations and 35 repetitions per point.

The two-tailed Student's t test was used for single comparisons of $ED_{50}$ values of naloxone. For multiple comparisons, analysis of variance with a post-test of Bonferroni was used. See, R. Miller, *Simultaneous Statistical Inference*, McGraw-Hill, N.Y. (1966).

EXAMPLE 1

Treatment with NTI and 5'-NTII.

NTI possesses antinociceptive activity; however, the dose used (10 pmol/mouse i.c.v.) in this study was the maximum dose at which selective antagonism at delta opioid receptors was observed without detection of antinociceptive activity. This equilibrium antagonist displayed an unusually long (18–24 hr) antagonist activity against delta opioid receptor agonists.

The dose of 5'-NTII used (10 nmol/mouse i.c.v.) was very large compared to that of NTI but, even at this dose, 5'-NTII displayed high selectivity for delta opioid receptors without any antinociceptive activity. Twenty-four hours (peak antagonist activity) after this dose of 5'-NTII, the $ED_{50}$ of DSLET, a specific delta-opioid receptor agonist ([D-Ser$^2$, Leu$^5$, Thr$^6$]enkephalin), is increased by 50-fold without affecting the $ED_{50}$s of mu or kappa opioid receptor agonists.

EXAMPLE 2

Effect of NTI on the development of morphine tolerance and dependence in mice treated acutely with morphine NTI (10 pmol/mouse) was administered i.c.v. 5.5 hrs before, and again just before the antinociceptive testing. Morphine sulfate (100 mg/kg) was administered s.c. 4 hrs before antinociceptive testing. When the drugs were used together, NTI was injected 90 min. before administration of morphine.

Figure 2:
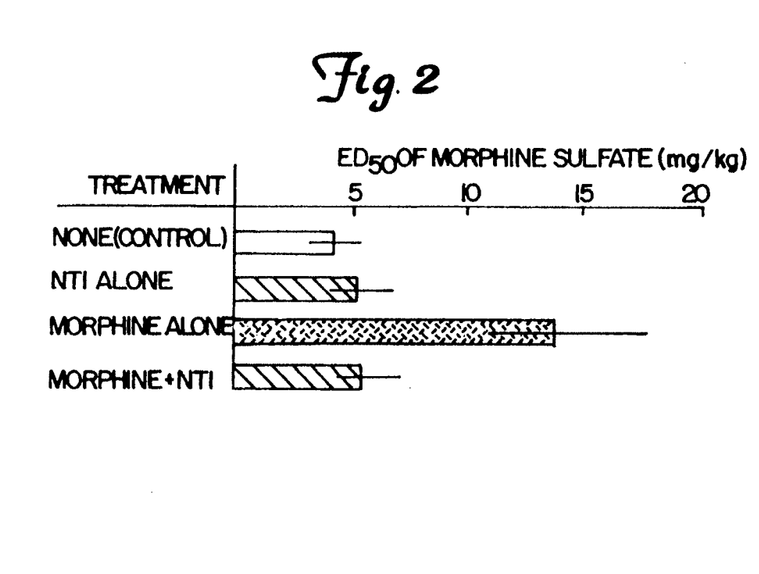
FIG. 2 is a graph depicting the effect of NTI on the development of tolerance in mice treated acutely with morphine. Bars represent 95% confidence limit (CL) of the $ED_{50}$ values.

As shown in FIG. 2, a single s.c. dose of 100 mg/kg of morphine sulfate produced acute tolerance several hours later that was manifested by an increase in the antinociceptive $ED_{50}$ (95% CL) of morphine sulfate [14(range=11–18) mg/kg] when compared to that of control animals [4.0(3.0–5.2) mg/kg]. Treatment with NTI alone did not alter the $ED_{50}$ of morphine sulfate [5.1(3.9–6.6) mg/kg]. However, NTI completely prevented the development of acute tolerance in mice treated with morphine and then evaluated for tolerance. These mice displayed an $ED_{50}$ of morphine sulfate of 5.6 (4.3–7.3) mg/kg which was not significantly different from the $ED_{50}$ of animals receiving NTI alone.

Mice that were injected with 100 mg/kg of morphine sulfate exhibited acute dependence several hours later as evidenced by the low dose of naloxone required to precipitate withdrawal jumping (Table 1).

TABLE 1

Effect of NTI on the Development of Physical Dependence in Mice Treated Acutely with Morphine

| Treatment | $ED_{50}$ of Naloxone[a] $\mu$mol/kg ± S.E. |
|---|---|
| Untreated controls | >250 |
| NTI (10 pmol i.c.v. 5.5 and 4 hr before the naloxone challenge) | >250 |
| Morphine sulfate (MS, 100 mg/kg, s.c. 4 hr before the naloxone) | 2.0 ± 0.3* |
| MS + NTI (10 pmol i.c.v. 90 min before MS) | 19.3 ± 6.3 |
| MS + NTI (10 pmol i.c.v. at the same time as MS) | 18.5 ± 1.8 |
| MS + NTI (10 pmol i.c.v. 90 min before and again at the same time as MS) | 90.2 ± 30.1* |

[a]Naloxone-induced withdrawal jumping was used to assess the degree of physical dependence (higher the degree of dependence the lower the dose of naloxone required to induce jumping).
*Values are significantly different from those of the MS + NTI (single injection) groups (analysis of variance + Bonferroni post-test).

Pretreatment of mice with a single dose of NTI either 90 min before or at the same time of inducing dependence with 100 mg/kg of morphine sulfate resulted in dependent mice that required about 10 times more naloxone to precipitate withdrawal jumping, indicating that these mice were much less physically dependent. When mice were pretreated twice with NTI before inducing dependence, the mice required 45 times more naloxone to precipitate withdrawal jumping, suggesting that the development of dependence was inhibited even further by the double treatment with NTI.

EXAMPLE 3

Effect of NTI and 5'-NTII on the Development of Morphine Tolerance and Dependence in Mice Treated Chronically with Morphine Mice were implanted with a single placebo (control) or morphine pellet (75 mg free base) for 3 days. NTI (10 pmol/mouse) was administered i.c.v. 90 min before and 24 and 48 hr after the morphine pellet implantation. 5'-NTII (10 nmol/mouse) was administered 24 hr before, at the same time as and 24 and 48 hr after the morphine pellet implantation.

Figure 3:
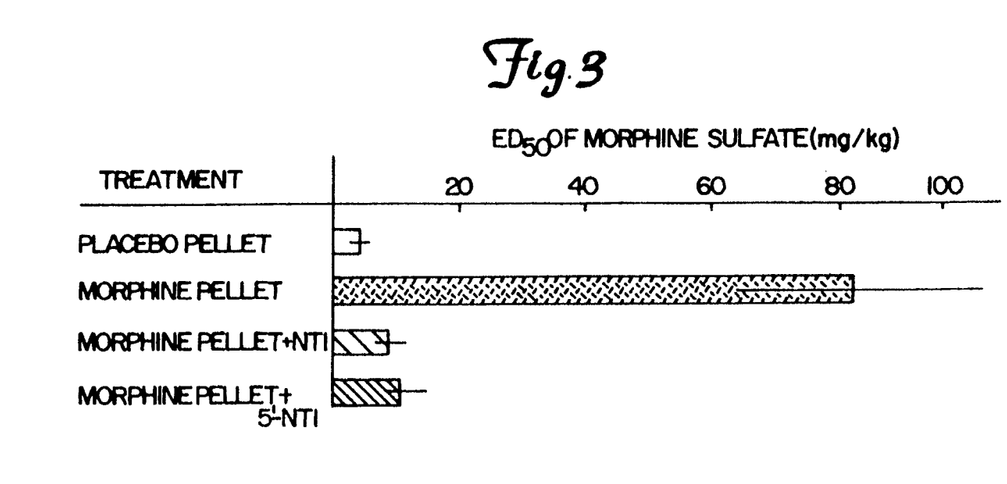
FIG. 3 is a graph depicting the effect of NTI and 5'-NTII on the development of tolerance in mice treated chronically with morphine. Bars represent 95% CL of the $ED_{50}$ values.

As shown in FIG. 3, implantation of morphine pellets for 3 days produced about a 19-fold increase of the $ED_{50}$ (95% CL) of morphine sulfate [82 (64–106) mg/kg] when compared to that [4.4 (3.4–5.6) mg/kg] of animals receiving placebo pellets. Animals that were treated with NTI or 5'-NTII together with morphine pellets displayed significantly lower $ED_{50}$ values of morphine sulfate [9.3 (7.1–11.9) and 11.7 (9.1–15.2) mg/kg, respectively] than that of the morphine-tolerant group which received morphine pellets alone. When compared to the $ED_{50}$ value of control animals, the $ED_{50}$ values of NTI- and 5'-NTII-treated mice represented only 2- and 3-fold increases, which suggested that the development of tolerance was suppressed substantially by the antagonists.

When the effect of NTI and 5'-NTII on the development of physical dependence was examined, similar findings to those of tolerance were observed. NTI suppressed the development of dependence substantially whereas 5'-NTII appeared to block it completely, as shown by the data on Table 2.

TABLE 2

Effect of NTI and 5'-NTII on the Development of Physical Dependence in Mice Treated Chronically with Morphine

| Treatment | $ED_{50}$ of Naloxone[a] $\mu$mol/kg ± S.E. |
|---|---|
| Control (s.c. placebo pellet implant for 3 days) | >250 |
| Morphine pellet (MP, s.c. implant for 3 days) | 0.05 ± 0.01 |
| MP + NTI (10 pmol i.c.v. 90 min before and 24 and 48 hr after MP) | 0.21 ± 0.03** |
| MP + 5'-NTII (10 nmol i.c.v. 24 hr before, at the same time as and 24 and 48 hr after MP) | >250 |

[a]Naloxone-induced withdrawal jumping was used to assess the degree of physical dependence (higher the degree of dependence the lower the dose of naloxone required to induce jumping).
**Value is significantly different (P<.01) from the MP alone group (two-tailed Student's t test).

EXAMPLE 4

Effect of NTI and 5'-NTII on Mu Opioid Receptors

It has been shown previously that both NTI and 5-NTII are highly effective antagonists against the activity of delta opioid receptor agonists with minimal or no effect on those of mu and kappa opioid receptor agonists (P. Portoghese et al., *Eur. J. Pharmacol.*, 146, 185 (1988); P. Portoghese et al., *J. Med. Chem.*, 33, 1547 (1990); *J. Med. Chem.*, 1714 (1990); M. Sofuogu et al., *J. Pharmacol. Exp. Ther.*, 257, 676 (1991)). To ensure that the doses of NTI and 5'-NTII used in the present experiments did not compromise the selectivity of the antagonists, especially via their possible interaction at mu opioid receptors, the effects of these antagonists on the antinociceptive activity of the highly selective mu opioid receptor agonist, DAMGO ([D-Ala², MePhe⁴, Gly-ol⁵] enkephalin) were studied. NTI (10 pmol/mouse) was administered 100 min before the i.c.v. injection of DAMGO and 20 min later, at the peak effect of DAMGO, the antinociceptive activity of the peptide was assessed. In another group of mice, NTI (10 pmol/mouse) was administered twice, once at 100 min before and again at the same time as the i.c.v. injection of DAMGO. 5'-NTII (10 nmol/mouse) was administered 24 hr before being tested with DAMGO.

Figure 4:
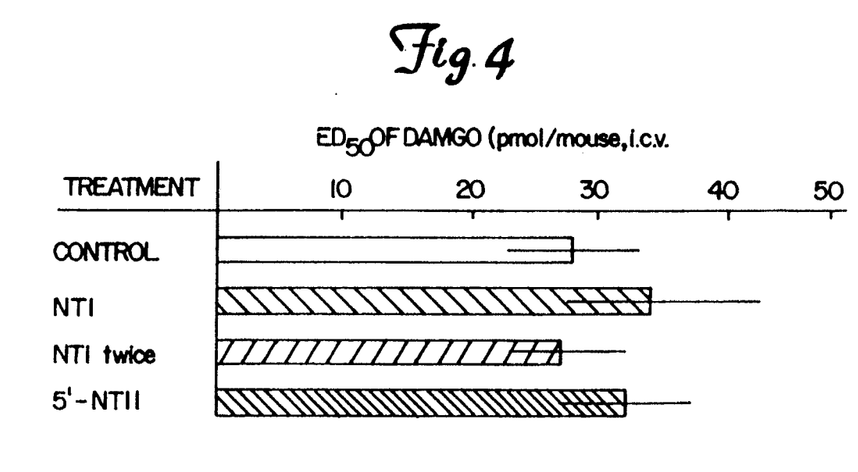
FIG. 4 is a graph depicting the effect of NTI and 5'-NTII on the antinociceptive action of DAMGO. Bars represent 95% CL of the $ED_{50}$ values.

As seen in FIG. 4, neither NTI nor 5'-NTII, at the dosages and injection protocol used, altered the antinociceptive activity of DAMGO.

The important role of mu opioid receptors in the development of opiate tolerance and physical dependence is well documented, particularly with the use of the selective, irreversible mu opioid receptor antagonist, β-FNA (β-funaltrexamine; see P. S. Portoghese et al., *J. Med. Chem.*, 23., 233 (1990); A. E. Takemori et al., *Eur. J. Pharmacol.* 70, 445 (1981); S. J. Ward et al., *J. Pharmacol. Ther.*, 220, 494 (1982)). β-FNA has been shown to inhibit the development of morphine tolerance and dependence in rats and to induce long-lasting withdrawal signs in monkeys. The dose of β-FNA used by DeLander et al., *J. Pharmacol. Exp. Ther.*, 231, 91 (1984) also significantly inhibited morphine-induced antinociception.

However, the involvement of delta opioid receptors in the development of these adaptive phenomena is less known. The availability of the highly potent and selective delta opioid receptor antagonists of formulas I, II and III, i.e., NTI and its nonequilibrium analogs, 5'-NTII have enabled direct examination in the whole animal, the involvement of delta opioid receptors in the development of tolerance to and physical dependence on morphine. Previously, it was reported that 5'-NTII possessed a long duration of action against delta agonists that lasted more than 48 hr, which is what one would expect from a non-equilibrium antagonist. Unexpectedly, the equilibrium antagonist, NTI, displayed an unusually long (18–24 hr) antagonist action against the antinociceptive effect of DSLET.

Examination of the data presented hereinabove demonstrates that the delta opioid receptor antagonists can markedly suppress the development of morphine tolerance and dependence in both the acute and chronic rat model. It is important to note that the antagonists at the dosages and injection schedules used had no influence on the activity of mu opioid receptor agonists such as DAMGO, a highly selective mu opioid receptor agonist. Preferably, the doses of delta opioid receptor antagonists used also do not affect the antinociceptive or "analgesic" activity of morphine. Thus, the inhibitory effect of NTI and 5'-NTII on the development of opiate tolerance and physical dependence appears to be due solely to their antagonist actions at delta opioid receptors. It follows then that delta, as well as mu, opioid receptors may be involved in the development of opiate tolerance and physical dependence. Thus, both opiate tolerance and physical dependence can be blocked in mammals by delta opioid receptor antagonists without compromising the antinociception or "analgesic" produced by drugs interacting at mu opioid receptors.

Selective blockage of delta opioid receptors by delta opioid receptor antagonists can suppress greatly the development of opiate tolerance and physical dependence without comprising the antinociceptive activity of drugs interacting at mu opioid receptors, such as DAMGO and particularly, morphine. The combined use of delta opioid receptor antagonists along with morphine-like analgesics can benefit the management of chronic pain.

All publications and patent applications are herein incorporated by reference to the same extent as if each individual publication or patent application was specifically and individually indicated to be incorporated by reference. It will be apparent to one of ordinary skill in the art that many changes and modifications can be made in the invention without departing from the spirit or scope of the appended claims.

What is claimed is:

1. A therapeutic method for treating opiate tolerance in a human undergoing opiate administration comprising administering to said human in need of such treatment an amount of a delta opioid receptor antagonist of the formula I:

wherein $R^1$ is $(C_1-C_5)$alkyl, $C_3-C_6$(cycloalkyl)alkyl, $C_5-C_7$(cycloalkenyl)alkyl, aryl, aralkyl, trans($C_4-C_5$)alkenyl, allyl or furan-2-ylalkyl, $R^2$ is H, OH or $O_2C(C_1-C_5)$alkyl; $R^3$ is H, $(C_1-C_5)$alkyl; or $((C_1-C_5)$alkyl)CO; X is O, S or NY, wherein Y is H or $(C_1-C_5)$alkyl; and $R^4$ and $R^5$ are individually H, F, Cl, Br, NCS, $NO_2$, $NH_2$, $(C_1-C_5)$alkyl or $(C_1-C_5)$alkoxy, or together are benzo; and the pharmaceutically acceptable salts thereof; wherein said amount is effective to block or reduce the tolerance of said human to an opioid mu receptor agonist.

2. The method of claim 1 wherein the opioid receptor agonist is selected from the group consisting of morphine, methadone, codeine, diacetyl morphine, morphine-N-oxide, oxymorphone, oxycodone, hydromorphone, hydrocodone, meperidine, heterocodeine, fentanyl, sufentanil, levo-acetylmethadol, alfentanil, levorphanol, tilidine, diphenoxylate, hydroxymorphone, noroxymorphone, metopon, propoxyphene, and the pharmaceutically acceptable salts thereof.

3. The method of claim 2 wherein said agonist is morphine, codeine or a pharmaceutically acceptable salt thereof.

4. The method of claim 1 wherein the amount of the compound of formula I is also effective to block or reduce the dependence of said human on said agonist.

5. The method of claims 1, 2 or 3 wherein the agonist is morphine or a pharmaceutically acceptable salt thereof.

6. The method of claim 1 wherein $R^1$ is methyl or $C_3-C_6$(cycloalkyl)alkyl and $R^2$=OH.

7. The method of claim 6 wherein $R^3$ is H.

8. The method of claim 7 wherein $R^1$ is cyclopropylmethyl.

9. The method of claim 1 wherein X is NH or O.

10. The method of claim 1 wherein $R^4$ and $R^5$ are H.

11. The method of claim 1 wherein $R^4$ is H and $R^5$ is 5'-NCS.

12. The method of claim 1 wherein the compound of formula I is naltrindole.

13. The method of claim 5 wherein the compound of formula I is naltrindole.

14. The method of claim 1 wherein the compound of formula I is naltrindole 5'-isocyanate.

15. The method of claim 5 wherein the compound of formula I is naltrindole 5'-isocyanate.

16. The method of claim 1 comprising administering the amount of the compound of formula I in a unit dosage form in combination with a pharmaceutically acceptable carrier.

17. The method of claim 16 wherein the pharmaceutically acceptable carrier is a liquid.

18. The method of claim 16 wherein the unit dosage form comprises a tablet, capsule or solution comprising the compound of formula I.

19. The method of claim 18 wherein the unit dosage form further comprises an effective amount of an opioid receptor agonist.

20. The method of claim 19 wherein the unit dosage form further comprises an effective amount of morphine or a pharmaceutically acceptable salt thereof.

21. The method of claim 1 wherein the amount of the compound of formula I is administered parenterally.

22. The method of claim 21 wherein the amount of the compound of formula I is administered by injection or by intravenous infusion.

23. The method of claim 1 wherein the amount of the compound of formula I is administered orally.

* * * * *

UNITED STATES PATENT AND TRADEMARK OFFICE
CERTIFICATE OF CORRECTION

PATENT NO. : 5,352,680

DATED : October 4th 1994

INVENTOR(S) : Portoghese et al.

It is certified that error appears in the above-identified patent and that said Letters Patent is hereby corrected as shown below:

Title page, item [57], ABSTRACT please delete "A motion provided " and insert --A method is provided--

In column 6, line 5 please delete "con, non" and insert --common--

In column 6, lines 10-20 part of the figure is missing, please see the drawing

In column 7, line 22 please delete "hydrazinc" and insert --hydrazine--

In column 7, line 32 please delete "hydrazinc" and insert --hydrazine--

In column 7, line 38 please delete "51" and insert --21--

Signed and Sealed this

First Day of July, 1997

*Attest:*

*Attesting Officer*

BRUCE LEHMAN

Commissioner of Patents and Trademarks